United States Patent [19]

Inbasekaran et al.

[11] Patent Number: 4,870,213
[45] Date of Patent: Sep. 26, 1989

[54] ARYLOXYPERFLUOROALKYL ARENES

[75] Inventors: Muthiah N. Inbasekaran; Ted A. Morgan, both of Midland, Mich.

[73] Assignee: The Dow Chemical Company, Midland, Mich.

[21] Appl. No.: 292,682

[22] Filed: Jan. 3, 1989

[51] Int. Cl.$^4$ ............................................. C07C 43/225
[52] U.S. Cl. .................................................. 568/645
[58] Field of Search ......................................... 568/645

[56] References Cited

U.S. PATENT DOCUMENTS

| | | | |
|---|---|---|---|
| 3,271,441 | 9/1966 | Brace | 260/476 |
| 3,944,558 | 3/1976 | Houghton et al. | 260/297 R |
| 4,423,249 | 12/1983 | Carl et al. | 568/655 |
| 4,727,187 | 2/1988 | Siegrist et al. | 564/89 |
| 4,737,509 | 4/1988 | Plummer | 514/386 |

OTHER PUBLICATIONS

V. C. R. McLoughlin and J. Thrower, "A Route to Fluoroalkyl–Substituted Aromatic Compounds Involving Fluoroalkylcopper Intermediates," *Tetrahedron*, vol. 25, pp. 5921–5940, (1969).

*Primary Examiner*—Donald B. Moyer
*Assistant Examiner*—Karen E. Kulesza
*Attorney, Agent, or Firm*—Paula Sanders Ruhr

[57] ABSTRACT

Aryloxyperfluoroalkyl arenes are disclosed which have relatively low melting points and pour points and are useful as high temperature lubricants. Examples of the invention include 1-(m-phenoxyphenoxy)-2-phenyl-1,1,2,2,-tetrafluoroethane and 1-(m-phenoxyphenoxy)-2-(m-trifluoromethylphenoxy-m-phenoxyphenoxy)-1,1,2,2-t etrafluoroethane.

7 Claims, No Drawings

ARYLOXYPERFLUOROALKYL ARENES

FIELD OF THE INVENTION

The present invention is related to perfluoroalkyl aromatic ethers. In particular, this invention is related to perfluoroalkyl aromatic ethers having utility as lubricants.

The use of polyphenyl ethers as lubricants for use in extreme environments has been explored for some time See, e.g., *Synthetic Lubricants*, Gunderson and Hart, editors, Reinhold Publishing Corp., New York (1962). Other compounds investigated as lubricants include perhalogenated alkoxy-s-triazines as taught in U.S. Pat. No. 3,525,745 to Anderson.

Current demands on lubricants include a need for lubricants which have low melting and pour points and which are also thermally and oxidatively stable at high temperatures.

SUMMARY OF THE INVENTION

The present invention is directed to compounds which meet these requirements, specifically aryloxyperfluoroalkyl arenes wherein an aromatic ring is attached to an oxygen molecule which is in turn attached to a perfluoroalkyl arene.

The compounds of the present invention are useful in tribochemical applications, as for example, high temperature lubricants. It is surprising that the compounds of the present invention have low pour points and melting points and are also thermally and oxidatively stable at high temperatures.

DETAILED DESCRIPTION OF ILLUSTRATIVE EMBODIMENTS

The compounds of the present invention are aryloxyperfluoroalkyl arene compounds corresponding to the formula:

$$Ar-O-(CF_2CF_2)_nAr' \qquad I$$

wherein Ar and Ar' are separately in each occurrence substituted or unsubstituted phenyl, biphenylyl, naphthyl, and substituted or unsubstituted heterocyclic compounds such as pyridyl, quinolinyl, pyrimidinyl, and triazenyl. Examples of substituents which may be present on the aromatic cores include perfluoroalkyl, perfluoroalkoxy, halogens, aryl, aryloxy, alkoxy, ester, alkyl, sulfones and ketones. Preferably, Ar and Ar' are each unsubstituted or, if substituted, contain an aryloxy substituent. The value of "n" is 1 to 5, most preferably about 1.

In a more preferred embodiment, the compound corresponds to the following formula

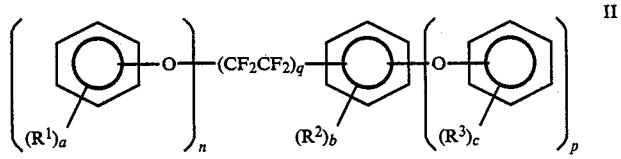

wherein $R^1$, $R^2$ and $R^3$ are separately in each occurrence perfluoroalkyl, perfluoroalkoxy, halogen, aryl, aryloxy, alkoxy, ester alkyl carbonyl, or sulfonyl: a, b, and c are separately in each occurrence zero to 5, preferably zero: n is 1 to 5, preferably 1, Q is 1 to 10 and p is zero to 10.

Examples of the compound of this invention include 1-(m-phenoxyphenoxy)-2-phenyl-1,1,2,2-tetrafluoroethane, 1-(m-phenoxyphenoxy)-2-(m-phenoxyphenoxyphenyl-1,1,2,2-tetrafluoroethane and 1-(m-phenoxyphenoxy)-2-(m-hydroxyphenyl-1,1,2,2-tetrafluoroethane and 1-(m-phenoxyphenoxy)-2-(m-trifluoromethylphenoxy-m-phenoxyphenoxy)-1,1,2,2-tetrafluoroethane.

In general, the compounds of the present invention are prepared by coupling aryloxyperfluoroalkyliodides and iodoarenes in a polar aprotic solvent in the presence of a catalyst at elevated temperatures. The general method is taught by McLoughlin and Thrower, *Tetrahedron* (1969) 25, 5921, hereby incorporated by reference.

Solvents useful in the preparation of the compounds of this invention include dioxane, pyridine, dimethylformamide, acetonitrile and dimethyl sulfoxide. Dimethylformamide and dimethyl sulfoxide are preferred with dimethyl sulfoxide being more preferred.

Examples of catalysts useful in the preparation of the compounds of this invention include copper and activated copper with activated copper being preferred.

The elevated temperatures useful in the preparation of the compounds of this invention are generally those temperatures over 50° C. and less than about 200° C. More preferably, the temperatures useful in the preparation of the compounds of this invention are at least about 110° C. and no greater than about 130° C.

The aryloxyperfluoroalkyliodides useful as starting materials in the preparation of the compounds of this invention may be prepared by the method taught by Carl and Ezzell in U.S. Pat. No. 4,423,249, hereby incorporated by reference. Generally, the aryloxyperfluoroalkyliodides are prepared by reacting a phenoxide with a 1,1-difluoro-1,2-dihaloethane in an organic solvent at temperatures ranging from about −30° C. to about 100° C.

The following examples are provided to illustrate the invention and should not be interpreted as limiting it in any way. Unless stated otherwise, all parts and percentages are by weight.

EXAMPLE 1

Preparation of 1-(m-phenoxyphenoxy)-2-phenyl-1,1,2,2-tetrafluoroethane

Potassium hydroxide (1.24 g, 87 percent pure, 19.3 mmoles) and m-phenoxyphenol (4 g, 21.2 mmoles) in 20 ml of toluene is stirred and refluxed under a Dean-Stark trap for one hour. The toluene-water azeotrope is removed over a one-hour period. A 14-ml portion of glyme is added to the dry potassium salt. Next, 1,2-diiodotetrafluoroethane (7.8 g, 20 mmoles) is added dropwise and the mixture is stirred at ambient temperature for 2 hours and then refluxed for 4 additional hours. The reaction mixture is then added to 100 ml of water with stirring and acidified with 6N HCl. The product is extracted 2×30 ml of ethyl acetate. The organic solution is dried using MgSO₄ and evaporated to remove the solvent. The product, 1-iodo-2-(m-phenoxyphenoxy)-1,1,2,2-tetrafluoroethane, is purified by flash chromatography on silica gel and its identity is confirmed by gas chromatography and mass spectrometry. Yield obtained is 26.7 percent based on m-phenoxyphenol and purity is 97.8 percent.

The 1-iodo-2-(m-phenoxyphenoxy)-1,1,2,2-tetrafluoroethane (2.06 g, 5 mmoles) is then mixed with iodobenzene (1.12 g, 5.5 mmoles), activated copper (0.7 g, 11 mmoles) and 20 ml dimethyl sulfoxide (DMSO) and heated to 120° C. The mixture is heated and stirred at 120° C. for 16 hours and then cooled, diluted with 100 ml water, acidified with HCl and the product is extracted with ethyl acetate (2×40 ml). A colorless oil, 1-(m-phenoxyphenoxy)-2-phenyl-1,1,2,2-tetrafluoroethane, is recovered in a yield of 69 percent based on 1-iodo-2-(m-phenoxyphenoxy)-1,1,2,2-tetrafluoroethane (1.3 g). The identity of the product is confirmed by mass spectrometry. The 1-(m-phenoxyphenoxy)-2-phenyl-1,1,2,2-tetrafluoroethane has a pour point of −23° C.

EXAMPLE 2

Preparation of 1-(m-phenoxyphenoxy)-2-(m-halophenyl)-1,1,2,2-tetrafluoroethane

Following the procedure described in Example 1, 10 mmoles of 1-iodo-2-(m-phenoxyphenoxy)-1,1,2,2-tetrafluoroethane and 20 mmoles of m-bromoiodobenzene in DMSO in the presence of 20 mmoles of activated copper is stirred and heated for 6 hours. The product, 1-(m-phenoxyphenoxy)-2-(m-halophenyl)-1,1,2,2-tetrafluoroethane is recovered as a colorless oil in a yield of 79 percent as described above. The ratio of bromine to iodine in the halophenyl group in the 2 position is 1 to 3.

EXAMPLE 3

Preparation of 1-(m-phenoxyphenoxy)-2-(m-phenoxyphenoxyphenyl)-1,1,2,2-tetrafluoroethane The potassium salt of m-phenoxyphenol is prepared from 1.2 g of m-phenoxyphenol and 0.4 g of potassium hydroxide in refluxing toluene with the azeotropic removal of water as described in Example 1. This salt and 1.6 g of 1-(m-phenoxyphenoxy)-2-(m-halophenyl)-1,1,2,2-tetrafluoroethane are reacted in 20 ml of refluxing pyridine in the presence of 0.5 g of cuprous chloride for 16 hours. Aqueous work-up and extraction with ethyl acetate followed by purification by flash chromatography yield 1.17 g of 1-(m-phenoxyphenoxy)-2-(m-phenoxyphenoxyphenyl)-1,1,2,2-tetrafluoroethane as a colorless oil. This represents a yield of 69 percent based on 1-(m-phenoxyphenoxy)-2-(m-halophenyl)-1,1,2,2-tetrafluoroethane. The purity of the product is 99 percent as confirmed by gas chromatography. The pour point of the 1-(m-phenoxyphenoxy)-2-(m-phenoxyphenoxyphenyl)-1,1,2,2-tetrafluoroethane is 0° C.

EXAMPLE 4

Preparation of 1-(m-phenoxyphenoxy)-2-(m-hydroxyphenyl)-1,1,2,2-tetrafluoroethane A mixture of 1-iodo-2-(m-phenoxyphenoxy)-1,1,2,2-tetrafluoroethane (3.08 g, 7.5 mmoles) and m-hydroxyiodobenzene (1.43 g, 6.5 mmoles) is heated in 5 ml of DMSO in the presence of 1.5 g of activated copper at 110° C. to 120° C. for 21 hours. The product is purified as described in Example 1 and is obtained in an overall yield of about 47 percent based on 1-iodo-2-(m-phenoxyphenoxy)-1,1,2,2-tetrafluoroethane.

EXAMPLE 5

Preparation of 1-(m-phenoxyphenoxy)-2-(m-trifluoromethylphenoxy-m-phenoxyphenoxy)-1,1,2,2-tetrafluorethane A potassium salt is obtained from 1 g (2.65 mmoles) of the phenolic derivative described in Example 4 and 200 mg of potassium hydroxide. This salt is mixed with 4 mmoles of m-(m-bromophenoxy)benzotrifluoride in 20 ml of refluxing pyridine in the presence of 200 mg of cuprous chloride for 16 hours. The product, a colorless oil, is purified as described in Example 1 It is 1-(m-phenoxyphenoxy)-2-(m-trifluoromethylphenoxy-m-phenoxyphenoxy)-1,1,2,2-tetrafluorethane obtained in a yield of 88 percent based on the phenolic derivative.

What is claimed is:

1. An aryloxyperfluoroalkyl arene of the formula:

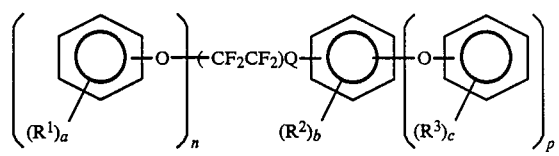

wherein $R^1$, $R^2$ and $R^3$ are separately in each occurrence perfluoroalkyl, perfluoroalkoxy, halogen, aryl, aryloxy, ester alkyl carbonyl, or sulfonyl; a, b, and c are separately in each occurrence zero to 5; n is 1–5, Q is 1–5 and p is zero to 10.

2. The compound of claim 1 wherein a, b and c are in each occurrence zero.

3. The compound of claim 1 which is 1-(m-phenoxyphenoxy)-2-phenyl-1,1,2,2-tetrafluoroethane.

4. The compound of claim 1 which is 1-(m-phenoxyphenoxy)-2-(m-phenoxyphenoxyphenyl)-1,1,2,2-tetrafluoroethane.

5. The compound of claim 1 which is 1-(m-phenoxyphenoxy)-2-(m-hydroxyphenyl-1,1,2,2-tetrafluoroethane.

6. The compound of claim 1 which is 1-(m-phenoxyphenoxy)-2-(m-trifluoromethylphenoxy-m-phenoxyphenoxy)-1, 1, 2, 2-tetrafluoroethane.

7. The compound of claim 1 which is 1-(m-phenoxyphenoxy)-2-(m-halophenyl)-1,1,2,2-tetrafluoroethane wherein halo is bromo or chloro.

* * * * *

UNITED STATES PATENT AND TRADEMARK OFFICE
CERTIFICATE OF CORRECTION

PATENT NO. : 4,870,213

DATED : September 26, 1989

INVENTOR(S) : Muthiah N. Inbasekaran; Ted A. Morgan

It is certified that error appears in the above-identified patent and that said Letters Patent is hereby corrected as shown below:

On the cover page, in the last 3 lines of the Abstract, "1-(m-phenoxyphenoxy)-2-(m-trifluoromethylphenoxy-m-phenoxyphenoxy)-1,1,2,2-t etrafluoroethane" should correctly appear as
-- 1-(m-phenoxyphenoxy)-2-(m-trifluoromethylphenoxy-m-phenoxyphenoxy)-1,1,2,2-tetrafluoroethane --.

Col. 1, line 55, that portion of the formula which reads "$(CF_2CF_2)_q$" should correctly appear as -- $(CF_2CF_2)_Q$ --.

Col. 4, line 35, that portion of the formula which reads "$(CF_2CF_2)Q$" should correctly appear as -- $(CF_2CF_2)_Q$ --;

line 44, -- alkoxy, -- should be inserted between "aryloxy" and "ester".

Signed and Sealed this

Sixth Day of November, 1990

*Attest:*

HARRY F. MANBECK, JR.

*Attesting Officer*  *Commissioner of Patents and Trademarks*